(12) United States Patent
Malhi

(10) Patent No.: US 9,174,043 B2
(45) Date of Patent: Nov. 3, 2015

(54) METHODS FOR SURGICAL WOUND DRESSING INCORPORATING CONNECTED HYDROGEL BEADS HAVING AN EMBEDDED ELECTRODE THEREIN

(71) Applicant: Covidien LP, Mansfield, MA (US)

(72) Inventor: Arnaz Malhi, Watertown, MA (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 14/527,004

(22) Filed: Oct. 29, 2014

(65) Prior Publication Data

US 2015/0057735 A1    Feb. 26, 2015

Related U.S. Application Data

(62) Division of application No. 12/850,683, filed on Aug. 5, 2010, now Pat. No. 8,900,217.

(60) Provisional application No. 61/231,370, filed on Aug. 5, 2009.

(51) Int. Cl.
*A61N 1/04* (2006.01)
*A61N 1/32* (2006.01)
(Continued)

(52) U.S. Cl.
CPC ............ *A61N 1/326* (2013.01); *A61F 13/0203* (2013.01); *A61F 13/0209* (2013.01); *A61F 13/0226* (2013.01); *A61L 26/008* (2013.01); *A61M 1/0088* (2013.01); *A61M 27/00* (2013.01); *A61N 1/0468* (2013.01); *A61N 1/24* (2013.01);
(Continued)

(58) Field of Classification Search
CPC ............ A61F 13/0203; A61F 13/0209; A61F 13/0213; A61F 13/0226; A61F 13/023; A61F 2013/00536; A61F 2013/0054; A61F 13/00068; A61L 26/008; A61M 1/0088; A61M 27/00; A61N 1/0468; A61N 1/205; A61N 1/24; A61N 1/326
See application file for complete search history.

(56) References Cited

U.S. PATENT DOCUMENTS

| 3,095,877 A | 7/1963 | Rowan |
| 4,490,005 A | 12/1984 | Hovey |

(Continued)

FOREIGN PATENT DOCUMENTS

| EP | 0853950 A1 | 7/1998 |
| EP | 1088569 A2 | 4/2001 |

(Continued)

OTHER PUBLICATIONS

US 7,186,244, 3/2007, Hunt et al. (withdrawn).

(Continued)

*Primary Examiner* — Adam Marcetich

(57) ABSTRACT

According to an embodiment of the present disclosure, a wound dressing system is presented. The wound dressing system includes a fluid permeable support layer, the support layer configured for positioning within a wound and adapted to generally conform to a topography of the wound, and to permit exudates from the wound to pass therethrough. The wound dressing system further includes a plurality of beads supported by the support layer, the beads defining an insulated inter-connected elongate member and an electrode embedded within and extending through at least a portion of the elongate member. Also, a current is generated by an external energy source that electrically flows through the electrode.

11 Claims, 4 Drawing Sheets

(51) Int. Cl.

| | | |
|---|---|---|
| *A61N 1/18* | (2006.01) | |
| *A61L 27/52* | (2006.01) | |
| *A61L 15/62* | (2006.01) | |
| *A61M 1/00* | (2006.01) | |
| *A61M 27/00* | (2006.01) | |
| *A61N 1/24* | (2006.01) | |
| *A61L 26/00* | (2006.01) | |
| *A61F 13/02* | (2006.01) | |
| *A61F 13/00* | (2006.01) | |
| *A61N 1/20* | (2006.01) | |

(52) U.S. Cl.
CPC ......... *A61F 13/00068* (2013.01); *A61F 13/023* (2013.01); *A61F 13/0213* (2013.01); *A61F 2013/0054* (2013.01); *A61F 2013/00536* (2013.01); *A61N 1/205* (2013.01)

(56) References Cited

U.S. PATENT DOCUMENTS

| | | |
|---|---|---|
| 4,892,516 A | 1/1990 | Harle |
| 5,288,289 A | 2/1994 | Haak et al. |
| 5,405,317 A | 4/1995 | Myers et al. |
| 5,451,204 A | 9/1995 | Yoon |
| 5,700,239 A | 12/1997 | Yoon |
| 5,756,127 A | 5/1998 | Grisoni et al. |
| 5,814,094 A | 9/1998 | Becker et al. |
| 5,833,642 A | 11/1998 | McCabe et al. |
| 5,958,465 A | 9/1999 | Klemm et al. |
| 5,974,344 A | 10/1999 | Shoemaker, II |
| 6,238,403 B1 | 5/2001 | Greene et al. |
| 6,345,623 B1 | 2/2002 | Heaton et al. |
| 6,398,767 B1 | 6/2002 | Fleischmann |
| 6,458,109 B1 | 10/2002 | Henley et al. |
| 6,488,643 B1 | 12/2002 | Turney et al. |
| 6,520,982 B1 | 2/2003 | Boynton et al. |
| 6,522,918 B1 | 2/2003 | Crisp et al. |
| 6,530,934 B1 | 3/2003 | Jacobsen et al. |
| 6,553,998 B2 | 4/2003 | Heaton et al. |
| 6,557,704 B1 | 5/2003 | Randolph |
| 6,626,891 B2 | 9/2003 | Ohmstede |
| 6,648,862 B2 | 11/2003 | Watson |
| 6,685,681 B2 | 2/2004 | Lockwood et al. |
| 6,695,823 B1 | 2/2004 | Lina et al. |
| 6,695,824 B2 | 2/2004 | Howard et al. |
| 6,752,794 B2 | 6/2004 | Lockwood et al. |
| 6,755,807 B2 | 6/2004 | Risk, Jr. et al. |
| 6,764,462 B2 | 7/2004 | Risk, Jr. et al. |
| 6,767,334 B1 | 7/2004 | Randolph |
| 6,800,074 B2 | 10/2004 | Henley et al. |
| 6,814,079 B2 | 11/2004 | Heaton et al. |
| 6,824,533 B2 | 11/2004 | Risk, Jr. et al. |
| 6,855,135 B2 | 2/2005 | Lockwood et al. |
| 6,855,860 B2 | 2/2005 | Ruszczak et al. |
| 6,856,821 B2 | 2/2005 | Johnson |
| 6,887,228 B2 | 5/2005 | McKay |
| 6,936,037 B2 | 8/2005 | Bubb et al. |
| 6,942,633 B2 | 9/2005 | Odland |
| 6,942,634 B2 | 9/2005 | Odland |
| 6,951,553 B2 | 10/2005 | Bubb et al. |
| 6,979,324 B2 | 12/2005 | Bybordi et al. |
| 6,994,702 B1 | 2/2006 | Johnson |
| 7,004,915 B2 | 2/2006 | Boynton et al. |
| 7,022,113 B2 | 4/2006 | Lockwood et al. |
| 7,070,584 B2 | 7/2006 | Johnson et al. |
| 7,070,609 B2 | 7/2006 | West |
| 7,077,832 B2 | 7/2006 | Fleischmann |
| 7,108,683 B2 | 9/2006 | Zamierowski |
| 7,117,868 B1 | 10/2006 | Hapuntich et al. |
| 7,117,869 B1 | 10/2006 | Heaton et al. |
| 7,125,391 B2 | 10/2006 | Joze et al. |
| 7,128,735 B2 | 10/2006 | Weston |
| 7,144,390 B1 | 12/2006 | Hannigan et al. |
| 7,195,624 B2 | 3/2007 | Lockwood et al. |
| 7,198,046 B1 | 4/2007 | Argenta et al. |
| 7,214,202 B1 | 5/2007 | vogel et al. |
| 7,216,651 B2 | 5/2007 | Argenta et al. |
| 7,401,413 B1 | 7/2008 | Nelson |
| 8,900,217 B2 | 12/2014 | Malhi |
| 2001/0031943 A1 | 10/2001 | Urie |
| 2001/0043943 A1 | 11/2001 | Coffey |
| 2002/0016577 A1 | 2/2002 | Ohmstede |
| 2002/0099408 A1 | 7/2002 | Marks et al. |
| 2002/0143286 A1 | 10/2002 | Tumey |
| 2002/0151836 A1 | 10/2002 | Burden |
| 2003/0093041 A1 | 5/2003 | Risk, Jr. et al. |
| 2003/0139794 A1 | 7/2003 | Jenney et al. |
| 2003/0208149 A1 | 11/2003 | Coffey |
| 2003/0212357 A1 | 11/2003 | Pace |
| 2003/0212359 A1 | 11/2003 | Butler |
| 2003/0212419 A1 | 11/2003 | West |
| 2003/0219469 A1 | 11/2003 | Johnson et al. |
| 2004/0006319 A1 | 1/2004 | Lina et al. |
| 2004/0015223 A1 | 1/2004 | Andino et al. |
| 2004/0030304 A1 | 2/2004 | Hunt et al. |
| 2004/0039391 A1 | 2/2004 | Argenta et al. |
| 2004/0039415 A1 | 2/2004 | Zamierowski |
| 2004/0064111 A1 | 4/2004 | Lockwood et al. |
| 2004/0064132 A1 | 4/2004 | Boehringer et al. |
| 2004/0073151 A1 | 4/2004 | Weston |
| 2004/0093026 A1 | 5/2004 | Weidenhagen et al. |
| 2004/0122434 A1 | 6/2004 | Argenta et al. |
| 2004/0249432 A1 | 12/2004 | Cohen |
| 2005/0004507 A1 | 1/2005 | Schroeppel et al. |
| 2005/0004508 A1 | 1/2005 | Sun et al. |
| 2005/0065484 A1 | 3/2005 | Watson, Jr. |
| 2005/0137539 A1 | 6/2005 | Biggie et al. |
| 2005/0246002 A1 | 11/2005 | Martinez |
| 2005/0261642 A1 | 11/2005 | Weston |
| 2005/0261643 A1 | 11/2005 | Bybordi et al. |
| 2006/0015087 A1 | 1/2006 | Risk, Jr. et al. |
| 2006/0025727 A1 | 2/2006 | Boehringer et al. |
| 2006/0041247 A1 | 2/2006 | Petrosenko et al. |
| 2006/0079852 A1 | 4/2006 | Bubb et al. |
| 2006/0100586 A1 | 5/2006 | Karpowicz et al. |
| 2006/0100594 A1 | 5/2006 | Adams et al. |
| 2006/0184246 A1 | 8/2006 | Zwirkoski |
| 2007/0021698 A1 | 1/2007 | Fleischmann |
| 2007/0027414 A1 | 2/2007 | Hoffman et al. |
| 2007/0032754 A1 | 2/2007 | Walsh |
| 2007/0032755 A1 | 2/2007 | Walsh |
| 2007/0032778 A1 | 2/2007 | Heaton et al. |
| 2007/0038172 A1 | 2/2007 | Zamierowski |
| 2007/0055209 A1 | 3/2007 | Patel et al. |
| 2007/0060862 A1 | 3/2007 | Sun et al. |
| 2007/0066946 A1 | 3/2007 | Haggstrom et al. |
| 2007/0073200 A1 | 3/2007 | Hannigan et al. |
| 2007/0078366 A1 | 4/2007 | Haggstrom et al. |
| 2007/0185463 A1 | 8/2007 | Mulligan |
| 2007/0225663 A1 | 9/2007 | Watt et al. |
| 2007/0260171 A1 | 11/2007 | Higuchi et al. |
| 2008/0065060 A1 | 3/2008 | Ein-Gal |
| 2008/0071207 A1* | 3/2008 | de Luis et al. .................. 602/47 |
| 2008/0103549 A1 | 5/2008 | Wenzel et al. |
| 2008/0188819 A1 | 8/2008 | Kloke et al. |
| 2008/0200857 A1 | 8/2008 | Lawhorn |
| 2008/0234641 A1 | 9/2008 | Locke et al. |
| 2008/0319371 A1 | 12/2008 | Etheredge et al. |
| 2009/0022941 A1 | 1/2009 | Fischer et al. |
| 2009/0024075 A1 | 1/2009 | Schroeppel et al. |
| 2009/0048642 A1 | 2/2009 | Goroszeniuk |
| 2009/0264809 A1 | 10/2009 | Sen |
| 2010/0036332 A1* | 2/2010 | Wolter .......................... 604/265 |
| 2010/0198174 A1 | 8/2010 | Hu et al. |
| 2010/0262091 A1 | 10/2010 | Larsson |
| 2010/0268177 A1* | 10/2010 | Hall et al. ..................... 604/313 |
| 2011/0046580 A1* | 2/2011 | Saitou .......................... 604/290 |

FOREIGN PATENT DOCUMENTS

| | | |
|---|---|---|
| EP | 1219311 A2 | 4/2002 |
| GB | 2307180 A | 5/1997 |
| GB | 2329127 A | 3/1999 |

(56) References Cited

FOREIGN PATENT DOCUMENTS

| | | |
|---|---|---|
| GB | 2336546 A | 10/1999 |
| GB | 2344531 A | 6/2000 |
| WO | WO 93/09727 A1 | 5/1993 |
| WO | WO 94/20041 A1 | 9/1994 |
| WO | WO 96/05873 A1 | 2/1996 |
| WO | WO 00/21586 A1 | 4/2000 |
| WO | WO 03/005943 A1 | 1/2003 |
| WO | WO 03/030966 A1 | 4/2003 |
| WO | WO 03/045492 A1 | 6/2003 |
| WO | WO 03/057070 A2 | 7/2003 |
| WO | WO 03/057071 A1 | 7/2003 |
| WO | WO 03/057307 A1 | 7/2003 |
| WO | WO 03/086232 A2 | 10/2003 |
| WO | WO 03/092620 A2 | 11/2003 |
| WO | WO 03/101508 A2 | 12/2003 |
| WO | WO 2004/018020 A1 | 3/2004 |
| WO | WO 2005/009488 A2 | 2/2005 |
| WO | WO 2007/092405 A2 | 8/2007 |
| WO | WO 2007/092405 A3 | 8/2007 |
| WO | WO 2007/120557 A2 | 10/2007 |
| WO | WO 2008104609 A1 * | 9/2008 ............ A61M 1/00 |
| WO | WO 2008131894 A1 * | 11/2008 |
| WO | WO 2009016605 A2 * | 2/2009 ............ A61L 15/42 |

OTHER PUBLICATIONS

Examiner's Report from counterpart Canadian Patent Application No. 2,770,182, dated Dec. 4, 2014, 3 pp.
Examiner's Report from counterpart Canadian Patent Application No. 2,770,182, dated Sep. 16, 2013, 2 pp.
International Search Report and Written Opinion of counterpart International Patent Application No. PCT/US10/44497, mailed Sep. 23, 2010, 11 pp.
Prosecution History from U.S. Appl. No. 12/850,683, dated Sep. 9, 2011 through Jul. 30, 2014, 103 pp.

* cited by examiner

METHODS FOR SURGICAL WOUND DRESSING INCORPORATING CONNECTED HYDROGEL BEADS HAVING AN EMBEDDED ELECTRODE THEREIN

CROSS-REFERENCE TO RELATED APPLICATIONS

This application is a divisional application of and claims the benefit of priority under 35 U.S.C. §120 to U.S. patent application Ser. No. 12/850,683, titled "Surgical Wound Dressing Incorporating Connected Hydrogel Beads Having an Embedded Electrode Therein," filed on Aug. 5, 2010, which claims the benefit of priority under 35 U.S.C. §119 to U.S. Patent Application No. 61/231,370, titled "Surgical Wound Dressing," filed on Aug. 5, 2009, each of which is incorporated herein by reference in its entirety for all purposes.

BACKGROUND

1. Technical Field

The present disclosure generally relates to an apparatus for treating an open wound and, more particularly, to a wound dressing system incorporating a plurality of beads, the beads defining an insulated connected elongate member having an embedded electrode therewith.

2. Discussion of Related Art

Wound closure involves the migration of epithelial and subcutaneous tissue adjacent the wound towards the center of the wound until the wound closes. Unfortunately, closure is difficult with large wounds or wounds that have become infected. In such wounds, a zone of stasis (i.e., an area in which localized swelling of tissue restricts the flow of blood to the tissues) forms near the surface of the wound. Without sufficient blood flow, the epithelial and subcutaneous tissues surrounding the wound not only receive diminished oxygen and nutrients, but, are also less able to successfully fight microbial infection and, thus, are less able to close the wound naturally. Such wounds have presented difficulties to medical personnel for many years.

Wound dressings have been used in the medical industry to protect and/or facilitate healing of open wounds. One technique has been to use negative pressure therapy, which is also known as suction or vacuum therapy. A variety of negative pressure devices have been developed to allow excess wound fluids, i.e., exudates, to be removed while at the same time isolating the wound to protect the wound and, consequently, effect recovery time. Various wound dressings have been modified to promote the healing of open wounds.

Issues that continually need to be addressed when using a wound dressing in negative pressure therapy include ease of use, efficiency of healing a wound, and sufficient drainage of wound exudates. One desire is to provide effective electrical stimulation or E-STIM therapy, by providing sufficient current flow to the wound bed of the wound dressing system, to transmit or flow current throughout the damaged tissue to enhance or promote a wound healing process.

Accordingly, a need exists for a system for providing a more consistent and uniform distribution of current to a wound bed of a wound dressing system while maintaining a moist wound environment.

SUMMARY

The present disclosure generally relates to an apparatus for treating an open wound.

According to an aspect of the present disclosure, a wound dressing system is provided and includes a fluid permeable cover layer configured for positioning across a wound, wherein the cover layer is configured to permit exudates from the wound to pass therethrough; a plurality of beads positionable in the wound and retained within the wound by the cover layer, the beads defining an insulated inter-connected elongate member; and an electrode embedded within and extending through at least a portion of the elongate member. In use, a current generated by an external energy source electrically flows through the electrode.

The wound dressing system may further include a conduit for supplying reduced pressure to the wound.

The plurality of beads may be constructed from hydrogel materials. The embedded electrode may extend through an entire length of the elongate member.

Each bead of the plurality of beads may have a first length, and adjacent beads of the plurality of beads may be separated from each other by a second length. The first length may be greater than the second length.

A portion of at least one bead of the plurality of beads may include a conductive coating. The conductive coating may be at least one of Ag, Ag/Cl, Cu, Au, carbon rubber, carbon film, and aluminum film.

The wound dressing system may further include a peripheral electrode and a rotator in operable communication with the peripheral electrode.

The wound dressing system may still further include a support layer secured to the peripheral electrode and configured to secure the peripheral electrode in position. The support layer may at least partially overlie the peripheral electrode and may be positioned along a periphery of the wound.

The wound dressing system may further include a voltage source embedded within the fluid permeable support layer. The voltage source may be positioned at one end of the elongate member. The voltage source may be positioned so as to divide the elongate member into at least two portions.

Each bead of the plurality of beads may be sufficiently rigid to facilitate passage of the exudates through spaces defined between adjacent beads.

According to another aspect of the present disclosure, a method of manufacturing a wound dressing configuration is provided. The method comprises the steps of providing a fluid permeable cover layer, wherein the cover layer is configured for positioning across a wound and is configured to permit exudates from the wound to pass therethrough; providing a plurality of beads positionable in the wound, the beads defining an insulated inter-connected elongate member; and providing an electrode embedded within and extending through at least a portion of the elongate member; wherein a current generated by an external energy source electrically flows through the electrode.

The method may further include the step of supplying reduced pressure to the wound.

The plurality of beads may be constructed from hydrogel materials. The embedded electrode may extend through an entire length of the elongate member.

Each bead of the plurality of beads may have a first length; adjacent beads of the plurality of beads may be separated from each other by a second length; and the first length may be greater than the second length.

A portion of at least one bead of the plurality of beads may include a conductive coating. The conductive coating may be at least one of Ag, Ag/Cl, Cu, Au, carbon rubber, carbon film, and aluminum film.

The method may further comprise providing a peripheral electrode and a rotator in operable communication with the peripheral electrode. The method may still further comprise providing a cover layer adapted for positioning across the wound to substantially enclose the beads within the wound. The method may further comprise the step of positioning the peripheral electrode at least partially along a periphery of the outer member.

The method may further include the step of embedding a voltage source within the fluid permeable support layer. The method may include the step of positioning the voltage source at one end of the elongate member. The voltage source may be positioned so as to divide the elongate member into at least two portions.

The plurality of beads may be sufficiently rigid to facilitate passage of the exudates through spaces defined between adjacent beads.

According to yet another aspect of the present disclosure, a method of using a wound dressing configuration is provided. The method includes the steps of placing a plurality of hydrogel beads in a wound, the beads (i) defining an insulated inter-connected elongate member and (ii) having an electrode embedded within and extending through at least a portion of the elongate member; placing a peripheral wound electrode on a person; attaching a cover layer over the wound so that the cover layer forms a barrier between the wound and an outside environment; communicating energy to the embedded electrode and the peripheral electrode; and monitoring the energy communicated to the embedded electrode and the peripheral electrode.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiment(s) given below, serve to explain the principles of the disclosure, wherein.

DETAILED DESCRIPTION

Figure 1:
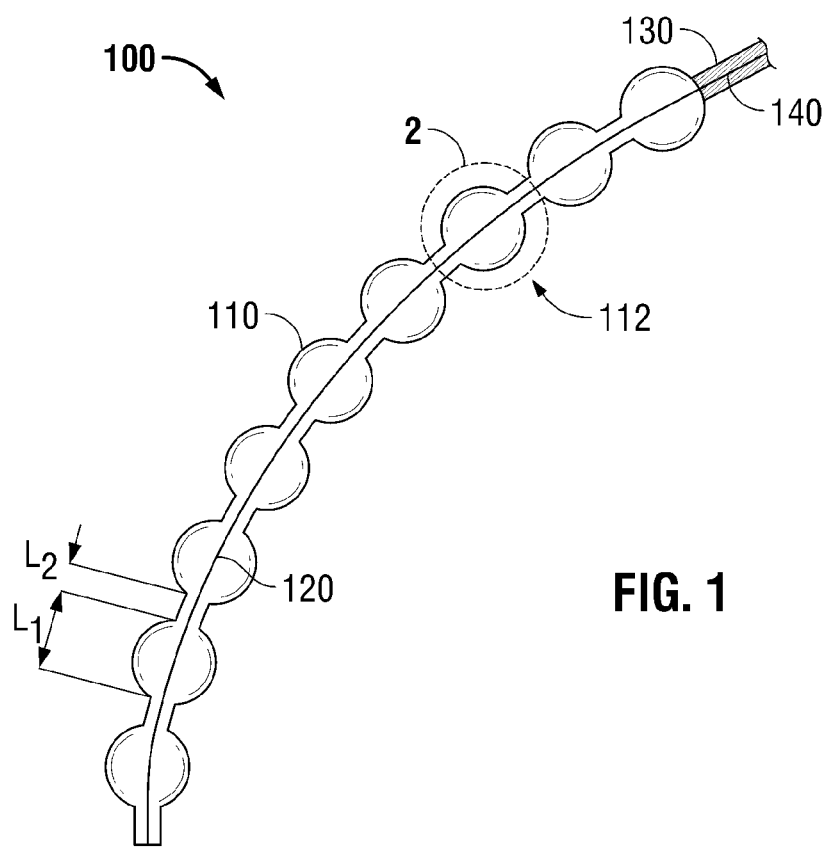
FIG. 1 is a diagram of an embodiment of a wound dressing system having a bead design including an electrode, in accordance with the present disclosure.

While embodiments of the present disclosure are susceptible to various modifications and alternative constructions, certain illustrated embodiments thereof have been shown in the drawings and will be described below in detail. It should be understood, however, that there is no intention to limit the embodiments of the present disclosure to the specific form disclosed, but, on the contrary, the embodiments are intended to cover all modifications, alternative constructions, and equivalents falling within the spirit and scope of the present disclosure as defined in the claims.

While various embodiments of the invention are described herein, it is to be distinctly understood that this invention is not limited thereto but may be variously embodied to practice within the scope of the following claims. The present invention may be understood more readily by reference to the following detailed description of the invention taken in connection with the accompanying drawing figures, which form a part of this disclosure. It is to be understood that this invention is not limited to the specific devices, methods, conditions or parameters described and/or shown herein, and that the terminology used herein is for the purpose of describing particular embodiments by way of example only and is not intended to be limiting of the claimed invention.

Prior to describing the present disclosure in further detail, it will first be helpful to define various terms that will be used throughout the following discussion. For example:

As used herein, the term "hydrogel" may refer to a wide variety of polymer-based compositions. These materials may be synthesized for example from monomer(s) or from monomer(s) mixed with polymer(s) in water. They may be obtained by chemical modification of existing polymer(s) or by adding water to existing dry polymers. Any biocompatible hydrogel may be utilized in accordance with the present disclosure. Generally speaking, a hydrogel according to the present disclosure may include a coherent, three-dimensional aqueous polymer system capable of imbibing water without liquefying. In embodiments, insolubility in water may be provided by crosslinking the hydrogel polymer. In embodiments, hydrogels or water-containing gels of the present disclosure may include water and various chemical substances.

The embodiments of the present disclosure further provide a wound dressing system that promotes healing of a wound that may be used in conjunction with negative pressure therapy. One exemplary wound dressing of the system includes a plurality of beads supported by a support layer. The beads conform to the shape of the wound while allowing the air and exudates to flow through the dressing, thereby promoting a moist environment and facilitating healing of the wound.

Various embodiments of the present disclosure provide negative pressure wound treatment (NPWT) systems (or apparatus) including a collection canister having a chamber to collect wound fluids. Embodiments of the presently disclosed NPWT systems are generally suitable for use in applying negative pressure to a wound to facilitate healing of the wound in accordance with various treatment modalities. Embodiments of the presently disclosed NPWT systems are entirely portable and may be worn or carried by the user such that the user may be completely ambulatory during the therapy period. Embodiments of the presently disclosed NPWT apparatus and components thereof may be entirely reusable or may be entirely disposable after a predetermined period of use or may be individually disposable whereby some of the components are reused for a subsequent therapy application.

Hereinafter, embodiments of the presently disclosed NPWT systems and embodiments of the presently disclosed beads for use in NPWT systems are described with reference to the accompanying drawings. Like reference numerals may refer to similar or identical elements throughout the description of the figures. As used herein, "wound exudate," or, simply, "exudate," generally refers to any fluid output from a wound, e.g., blood, serum, and/or pus, etc. As used herein, "fluid" generally refers to a liquid, a gas or both.

Embodiments will be described below while referencing the accompanying figures. The accompanying figures are merely examples and are not intended to limit the scope of the present disclosure.

Referring now to the drawings wherein like components are designated by like reference numerals throughout the several views, as seen in FIG. 1, a wound dressing system, according to an embodiment of the present disclosure, is generally designated as 100.

Wound dressing system 100 may be in the form of a beaded design including a plurality of hydrogel 110 beads (or hydrogel materials 110), a wound electrode 120, an insulating member 130, and a conducting wire 140.

Beads 110 define an inter-connected elongate member 112 supporting or surrounding an embedded wound electrode 120. Wound electrode 120 extends the entire length of elongate member 112. One end of wound electrode 120 is configured to connect to a conducting wire 140. Conducting wire 140 receives a current from an external energy source (not shown). The external energy source may be any type of energy source contemplated by one skilled in the art, such as, but, not limited to, a battery, fuel cell, generator, and/or hybrid power supply. Additionally, conducting wire 140 is surrounded by an insulating member 130.

Beads 110 may have a length or diameter $L_1$, and adjacent beads 110 may be separated from each other by a length $L_2$. It is further contemplated that length $L_1$ is greater than length $L_2$. However, any desirable distance/length relationship may be established between lengths $L_1$ and $L_2$ of adjacent beads 110.

Beads 110 may be formed to be substantially rigid so as to maintain their shapes for at least a predetermined period of time during a healing of a wound. In this regard, beads 110 when arranged within a wound bed "w" (shown in FIG. 4B) define interstitial spaces, pockets, or passages 492 (shown in FIG. 4B) therebetween to permit wound exudate to pass or migrate through passages 492. The sizes or diameters, $L_1$, of beads 110 can vary, but they should be sized to achieve a proper pore size through a bead arrangement to facilitate cell proliferation and allow fluid and air to be evacuated from the wound. Porosity in the range of 10-1000 µm has been found beneficial in stimulating cell proliferation and in allowing fluid and air to be evacuated from the wound. As a negative pressure is applied to wound bed "w," beads 110 may move and readjust their respective positions to prevent painful ingrowth that can occur with current foam designs.

Beads 110 may desirably remain substantially rigid for at least a predetermined period of time during healing so as to maintain the desired spacing of passages 492 therebetween. Beads 110 may be non-absorbable, partially absorbable or fully absorbable. If beads 110 are formed from an absorbable material, the rate of absorption of beads 110 may be selected to maintain the desired rigidity of beads 110 during a predetermined period of healing. One skilled in the art may select the materials of fabrication of beads 110 to reach these objectives.

The dissolution rate of beads 110 may be dependent on material selection, bead size (surface area of bead in contact with fluids), amount of fluid in wound bed "w" temperature and exposure to mechanical stress (i.e., compressive forces). Some or all of beads 110 could be designed to remain rigid for the entire time that the dressing remains in place on the patient, or from about 1 day to about 1 week or longer. This maintains air and fluid flow away from the wound bed "w." Some of beads 110 could be designed to dissolve over this time period, to release any active ingredients or agents incorporated therein. Additional dissolution of beads 110 could be timed to coincide with planned dressing changes to limit the potential of tissue growth into beads 110 and causing trauma upon removal of dressing.

Beads 110 may be made from a hydrogel material or the like. The hydrogel may be made from, for example, but not limited to, Promeon RG-63B hydrogel (available from Tyco Healthcare Group LP d/b/a Covidien).

Beads 110 may be manufactured from a suitable biocompatible material. Beads 110 may be antimicrobial beads, beads with growth factors, medicaments, antibiotics, analgesics, and healing factors such as vitamins, nutrients and the like. These beads 110 are preferably non-adherent and may be bio-absorbable over a predetermined period of time. Acrylic (PMMA) can be used for its clarity and would also provide the ability for the clinician to see the wound without removing the dressing. Other materials that could be used are polycarbonate, polystyrene, PVC, ABS, SAN, glass or silicone. Bio-absorbable polymers could also be used, e.g., polylactide (PLA), polyglycolide (PGA), Chitosan, polyethylene oxide (PEO) or polyethylene glycol (PEG).

Hydrogel is desirably used for beads 110 as it forms a conductive medium between wound electrode 120 and wound bed "w," thus facilitating a flow of current therebetween while maintaining a moist wound environment. In general, hydrogels consist of a hydrophilic network structure retaining high concentrations of water. Moreover, in this application, the hydrogel of beads 110 acts as a wound filler material as well since it helps retain and transport exudate coming out of the wound, while providing a conductive path for current flow.

Another example of a composition that can be used in this application is poly(vinyl alcohol) (PVA) since it is biocompatible and can be tailor made to provide good mechanical properties such that it does not disintegrate when placed in the wound. Since hydrogel may also be functioning as a conductive medium, a gel electrolyte may be most desirable. Experimentation with several materials has demonstrated that a poly(ethylene glycol) (PEG):PVA:NH4SCN composite gel electrolyte which has high ionic conductivity would be advantageous. Some other examples of similar gel electrolytes include poly(VC-AN), poly(MMA-VC), poly(styrene-AN), and poly(styrene-butadiene).

The design of beads 110 presents many advantages. For example, beads 110 may prevent direct contact of wound bed "w" with wound electrode 120. Each bead 110 may have a substantially circular/elliptical cross-sectional profile. The arrangement of beads 110 of wound dressing system 100 increases the contact area with wound bed "w," thus enabling the flow of current to a larger area of wound bed "w." This provides a more uniform distribution of current to the wound bed "w," which is one of the challenges in providing effective E-STIM therapy.

The size of beads 110 may be small enough such that multiple beads 110 would contact the wound bed "w" to achieve this objective. Additionally, the arrangement of beads 110 of wound dressing system 100 may aid in creating interstitial spaces (shown in FIG. 4B) so as to allow breathability through or around wound electrode 120. This can be easily achieved by ensuring length $L_1$ is greater than length $L_2$. The relatively thinner or shorter sections or lengths between beads 110 allow more flexibility as wound electrode 120 is twirled, folded-over, twisted, and placed by, for example, a clinician to fill up the wound.

In one embodiment, a number of wound electrodes 120 may be positioned or deposited at various preselected locations throughout the length of elongate member 112 of beads 110. Additionally, the length or diameter, $L_1$, of beads 110 may be of any size (from a few millimeters to a few inches). Also, the length of a bead 110 need not be equal to the diameter of said bead 110.

Wound electrodes 120 may be of any shape or size or width or length depending on the desired application. For example, wound electrode 120 may be a mesh design that envelops the interior of beads 110. In other words, wound electrode 120 need not be centrally disposed within beads 110 of elongate member 112. Wound electrode 120 may also be of uniform or non-uniform thickness as it extends through elongate member 112. It is contemplated that, a plurality of electrode placement schemes with more or fewer electrodes in different positions can be used. If a different electrode placement scheme is desired, wound electrode 120 and peri-wound electrode 340 (see FIGS. 3, 4A, and 4B) can be positioned differently as desired.

In one embodiment, the present disclosure may relate to a patient monitoring system which provides enhanced functional capability relative to known systems and provides a wireless communication link between a patient monitoring device, worn by a patient, and a local hub. The patient monitoring system may be adapted to monitor various patient physiological characteristics. The data from the patient monitoring device may be wirelessly transmitted to a local hub, which, in turn, is configured to automatically transfer the data to a remote server or computer (e.g., of a clinician), for example, over a public or private communications network.

In one embodiment, wound electrode 120 may be separately fabricated (as separate units) with respect to beads 110 and then combined to form a single unit. In an alternate embodiment, wound electrode 120 may be fabricated with beads 110 as one unit or component. Several separate or unitary fabrication techniques may be contemplated by one skilled in the art.

Figure 2:
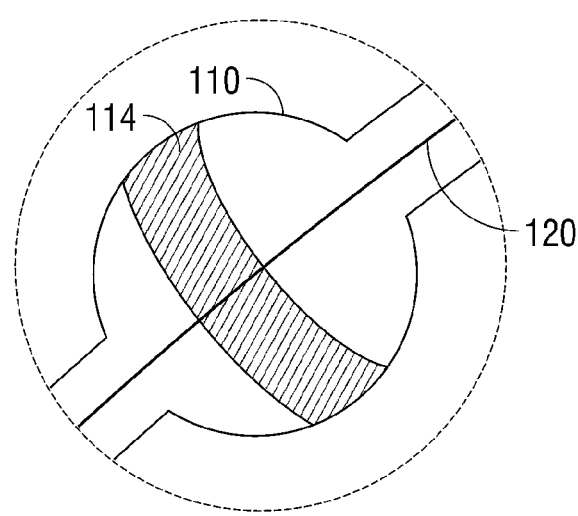
FIG. 2 is an enlarged diagram of the indicated area of detail of the wound dressing system of FIG. 1, illustrating a hydrogel bead including a conductive coating, in accordance with the present disclosure.

Referring now to FIG. 2, a diagram of an embodiment of a hydrogel bead including a conductive coating or outer surface, in accordance with the present disclosure is illustrated.

As described above, bead 110 is made from hydrogel material and includes wound electrode 120 embedded therein and extending therethrough. Each bead 110 may include conductive material(s) 114 disposed on an outer surface thereof. Each bead 110 may be of any uniform or non-uniform shape or size and may be positioned on any portion of wound electrode 120 depending on the desired application.

In one embodiment, each bead 110 may include conductive material(s) (e.g. Ag, Ag/AgCl, Cu, Au) coated on at least a portion of the outer surface thereof to enable enhanced current flow to specific parts of wound bed "w" (shown in FIG. 4B), such as the approximate center of the wound bed "w."

In one embodiment, only a select number of beads 110 of the total number of beads of wound dressing system 100 may incorporate a conductive coating 114. Alternatively, all beads 110 of the plurality of beads may incorporate a conductive coating 114. In additional alternate embodiments, a portion of the surface of beads 110 may include one type of conductive coating 114 (e.g., Ag) and another portion of the surface of beads 110 may include a different type of conductive coating (e.g., Ag/AgCl). Thus, different combinations of conductive coatings 114 may be used on the same elongate member 112 defining a plurality of different beaded segments.

In another embodiment, conductive coating 114 may at least partially envelop/encompass/engulf the outer surface of bead 110. As illustrated in FIG. 2, conductive coating 114 has a strip shape. However, any uniform or non-uniform shape and/or size or a design/pattern may be contemplated. In an alternate embodiment, a first portion of a bead 110 may be fully enveloped by one or more conductive coatings 114, whereas a second portion of bead 110 may be partially enveloped by one or more conductive coatings 114.

Figure 3:
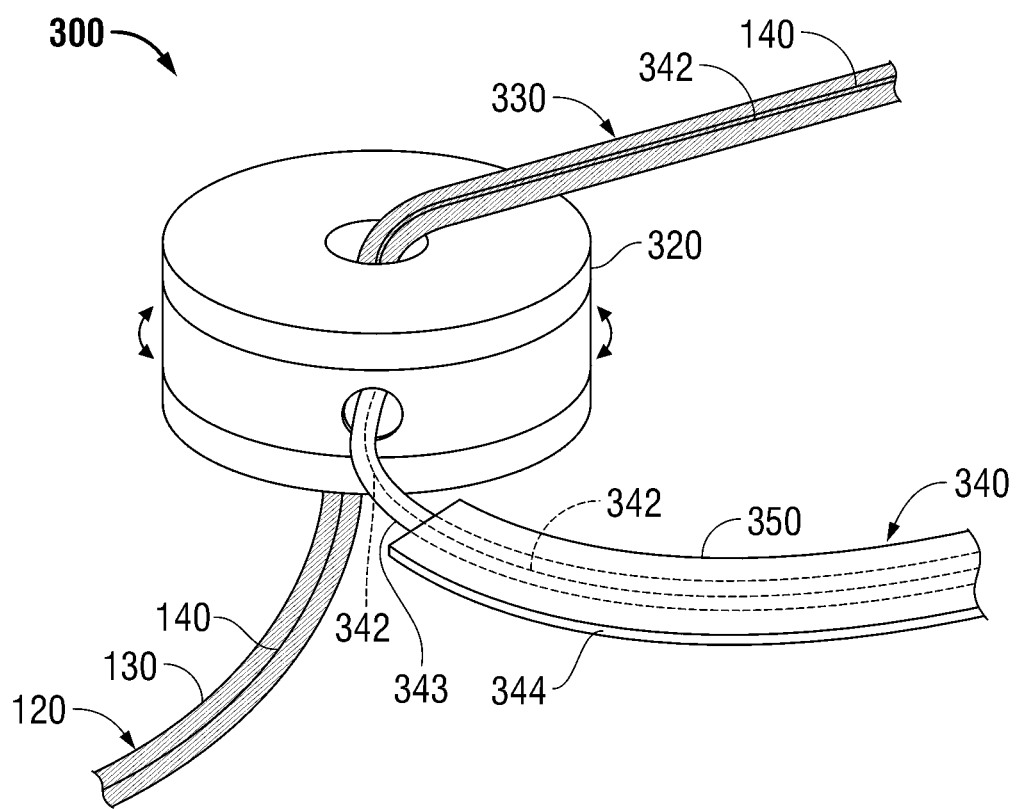
FIG. 3 is a diagram of an embodiment of a strain relief assembly of the wound dressing system of FIG. 1, in accordance with the present disclosure.

Referring now to FIG. 3, a strain relief or rotator system, in accordance with the present disclosure is illustrated, and generally designated as 300.

Rotator system 300 includes a rotator 320, an insulated connecting wire 330 (pig-tailed insulated conducting wires 140, 342) extending from the rotator 320, a peripheral wound electrode 340 extending from rotator 320, and a support layer 350 surrounding peripheral wound electrode 340.

Peripheral wound electrode 340 (also referred to herein as "peri-wound electrode") includes an electrode portion or conducting wire 342 having an insulating sheath 343 and having the insulating support layer 350 extending along a length thereof. Peri-wound electrode 340 may be available with or without a hydrogel layer between the peri-wound electrode 340 and the skin. The hydrogel layer can enhance contact with intact skin, hence enabling better current flow.

Support layer 350 includes an adhesive layer 344 (see FIG. 4B) on the bottom surface thereof to allow for easy fixation on the peri-wound area (shown in FIG. 4A) or around wound bed "w." Support layer 350 is fabricated from an insulation material to help ensure that the current flow is through the tissue. Support layer 350 may be constructed from common materials such as cloth, spun lace, vinyl, tricot, or other materials used to cover layers of common wound dressings such as PolySkin II (Tyco Healthcare Group LP d/b/a Covidien).

Materials used for peri-wound electrode 340 may be the same as that used for wound electrode 120. In an embodiment, support layer 350 and peri-wound electrode 340 are combined in the form of a silver printed cloth, which provides excellent current dispersion.

Both wound electrode 120 and peri-wound electrode 340 may be made out of materials commonly used for this purpose, e.g., Ag, AgCl, Au, Cu, Carbon Rubber, Carbon film, Aluminum film. Electrodes 120, 340 may be encapsulated in a conductive material or salt to either ensure good adhesion or improved conduction between hydrogel of beads 110 and peri-wound electrode 340 (e.g., by coating a silver electrode with AgCl (silver-chloride), or by providing a silver coated carbon electrode, etc.).

Both wound electrode 120 and peri-wound electrode 340 may be consolidated inside a plastic strain relief 320 (referred herein as "rotator") to enable easy management of dressing when in use. Rotator 320 permits rotational movement, thus providing strain relief and providing an easy means to apply both electrodes 120, 340. Conducting wires 140 and 342 (one going to each electrode 120, 340, not shown) may each be sheathed in insulation and may be pig-tailed to form connecting wire 330. Connecting wire 330 may extend to a connector 460 (shown in FIG. 4A) located within or in proximity to rotator 320, which enables easy connection and disconnection. Snap features common in medical electrodes (e.g., TENS electrodes mfg. by Tyco Healthcare Group LP d/b/a Covidien) may be used. Thus, conducting wire 140 leading to wound electrode 120, and conducting wire 342 leading to peri-wound electrode 340 are electrically insulated from each other. However, in an embodiment, elongate member 112 of wound electrode 120 is extendable through rotator 320, is supported on a cover layer 150, and surrounded by peri-wound electrode 340.

Figure 4A:
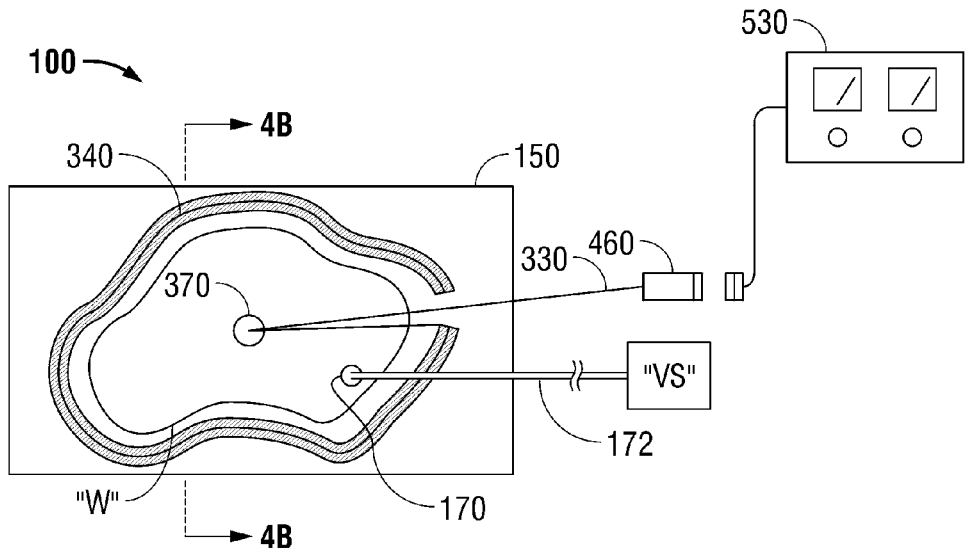
FIG. 4A is a top, plan view of wound dressing system of FIGS. 1-3, in accordance with the present disclosure.
Figure 4B:
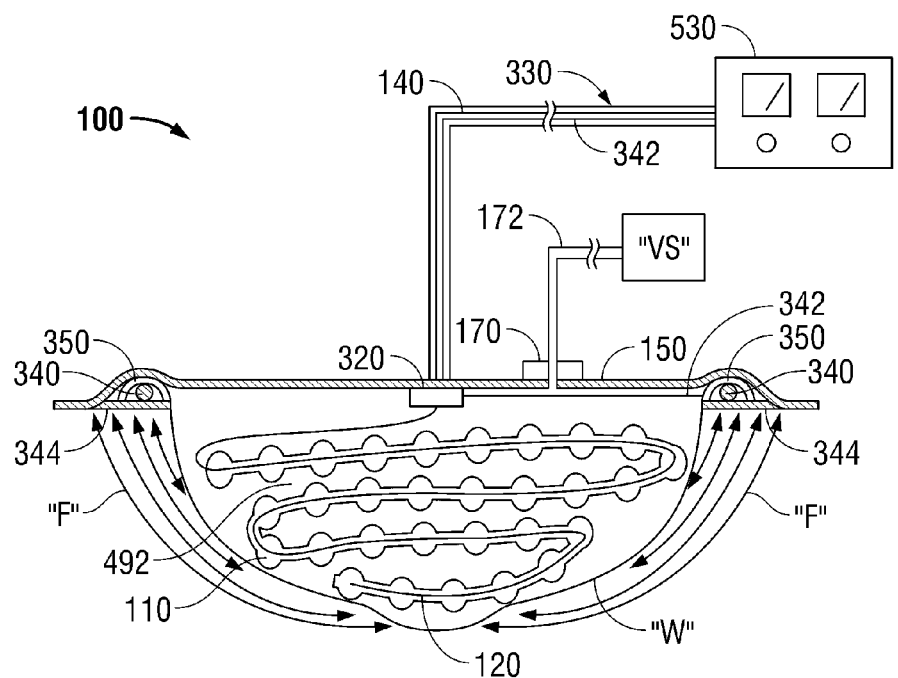
FIG. 4B is a cross-sectional view of the wound dressing system of FIG. 4A, as taken through 4B-4B of FIG. 4A.

Referring now to FIGS. 4A and 4B, a method of using an applying wound dressing system 100, illustrating a positioning of wound electrode 120 and peri-wound electrode 340, in accordance with the present disclosure, is depicted.

As seen in FIGS. 4A and 4B, wound dressing system 100 is shown in place in a wound bed "w." Wound bed "w" is circumferentially surrounded by peri-wound electrode 340 that is in contact with the tissue of the patient that is surrounding wound bed "w." Support layer 350 may overlie peri-wound electrode 340. Additionally, wound bed "w" is at least partially filled with a length of wound electrode 120.

As seen in FIGS. 4A and 4B, wound dressing system 100 includes cover layer 150 covering/isolating wound bed "w." Wound electrode 120 of system 100 is positioned within wound bed "w" and peri-wound electrode 340 of system 100 is positioned on the outer circumference or along an outer periphery of wound bed "w." Cover layer 150 is sized to overlie wound bed "w" and peri-wound electrode 340. Rotator 320 is supported by cover layer 150 to permit passage of wound electrode 120 into wound bed "w." Wound bed "w" is filled with would electrode 120 such that wound electrode 120 sits on the surface of wound bed "w," and beads 110 are arranged within wound bed "w," to define spaces or passages 492 therebetween to permit wound exudate to pass through passages 492.

Cover layer 150 is adapted to substantially overlie and enclose or cap wound bed "w," as shown in FIG. 4B. In an embodiment, it is contemplated that cover layer 150 may be substantially porous to permit exudates to pass from the wound bed "w" through cover layer 150. "Porous" as used herein refers to a material which contains numerous small perforations or pores which allow wound fluids of all kinds to pass through the material, Cover layer 150 may also be non-adherent. "Non-adherent" as used herein refers to a material that does not adhere to tissues in and around wound bed "w." This configuration allows fluid and exudates to flow uninhibited through the entire surface of cover layer 150 with minimal "sticking" of cover layer 150 to wound bed "w" thereby permitting a vacuum to be delivered over the entire surface of cover layer 150.

The passage of wound exudates through cover layer 150 is preferably unidirectional such that wound exudates do not flow back into wound bed "w." This unidirectional flow feature could be in the form of directional apertures imparted into the material layer, a lamination of materials of different absorption to cover layer 150 or specific material selection that encourages directional flow. However, a bidirectional layer for the purposes of supplying medicine or anti-infectives to wound bed "w" is also envisioned.

The sealing mechanism, for sealing or adhering cover layer 150 around wound bed "w," may be any adhesive applied to the tissue that surrounds wound bed "w." The adhesive should provide acceptable adhesion to the tissue surrounding wound bed "w," e.g., the peri-wound area, and be acceptable for use on the skin without contact deteriorization (e.g., the adhesive should preferably be non-irritating and non-sensitizing). The adhesive may be permeable to permit the contacted skin to breathe and transmit moisture. Additionally, the adhesive could be activated or de-activated by an external stimulus such as heat or a given fluid solution or chemical reaction. Adhesives include, for example, medical grade acrylics like the adhesive used with CURAFOAM ISLAND™ dressing of Tyco HealthCare Group LP d/b/a Covidien, or any silicone or rubber based medical adhesives that are skin friendly and non-irritating.

Cover layer 150 may typically be a flexible material, e.g., resilient or elastomeric, that seals the top of wound bed "w." Exemplary flexible materials include the transparent dressing manufactured under the trademark Polyskin II by Tyco Healthcare Group LP d/b/a Covidien. Preferably, cover layer 150 is transparent and provides a barrier to microbes and fluid containment. Cover layer 150 may be manufactured from a permeable plastic film providing it with a high moisture vapor transmission rate (MVTR) to allow the passage of exudates through the film. Such films could be manufactured from polyurethanes, breathable polyolefins, or copolyesters. The transparency of cover layer 150 permits a visual review of the status of the healing of wound "w." Alternatively, cover layer 150 may be impermeable to moisture vapors.

In use, beads 110 of wound electrode 120, disposed within wound bed "w" arrange themselves to conform to the shape of wound bed "w." In particular, beads 110 migrate into remote areas of the wound, i.e., "tunnel" into wound "w" as shown in FIG. 4B. Cover layer 150 is placed in contact with peripheral skin of the patient and may be secured thereto adhesives or the like. As seen in FIGS. 4A and 4B, a vacuum connector 170 may then be secured to cover layer 150 and a conduit 172 may then be connected to vacuum connector 170. A negative pressure source "VS" may then be activated, thus creating a reduced pressure state within wound bed "w." As the pumping progresses, beads 110 maintain their shape thereby creating and/or maintaining passageways 492 for the wound exudates to flow out of wound bed "w."

In further use, beads 110 of wound electrode 120 may be configured such that it enables easy application because of the flexible electrode configuration. It is intended that, for example, the clinician first places beads 110 of wound electrode 120 in wound bed "w" by twirling, twisting, or folding the same in order to fill wound bed "w." Gauze dipped in saline (e.g., Kerlix AMD mfg. by Tyco Healthcare Group LP d/b/a Covidien) can also be placed in wound bed "w" between layers of beads 110 to help manage and transport exudate.

Following filling of wound bed "w" with wound electrode 120, the clinician can place pen-wound electrode 340 around wound bed "w." Peri-wound electrode 340 is placed by peeling off a covering layer to expose an adhesive layer 344 (which is on the bottom side of support layer 350) and using it to affix peri-wound electrode 340 to intact skin of a patient. Since pen-wound electrode 340 is preferably flexible, the user can apply pen-wound electrode 340 such that it follows the peripheral contours of wound bed "w."

Wound electrode 120 and peri-wound electrode 340 do not need to be pre-cut into various shapes because both electrodes 120, 340 can be easily made to fit the contours of wound and pen-wound areas. The only dimension of wound electrode 120 that requires management by a clinician is the electrode length. If either wound/peri-wound electrode 120, 340 is too long, any length that is not required can be snipped with scissors at the distal end. Snipping with scissors is easy and intuitive, and is very commonly used by clinicians to help size wound dressing components for a particular wound.

Additionally, cover layer 150 is attached over wound bed "w" using an adhesive layer 344 so that it forms a barrier between wound bed "w" and an outside environment. Cover layer 150 can also extend over support layer 350 that was used to affix pen-wound electrode 340, hence reducing the possibility of support layer 350 peeling away. As cover layer 150 is being placed over wound bed "w," the clinician ensures that conducting wire 140 of wound electrode 120 comes out of wound bed "w" through rotator system 300 so as to allow communication with a voltage source (described with reference to FIGS. 5A and 5B).

With wound dressing system 100 in position as described above, a clinician activates voltage source 530 and vacuum source to a predetermined treatment setting. When voltage source 530 is activated, electrical current is delivered from voltage source 530 to wound electrode 120, into the tissue defining wound bed "w," to pen-wound electrode 340 and back to voltage source 530, and/or vice-versa depending on the setting. In this manner, an electrical circuit is formed to circulate electrical current (as indicated by arrows "F" of FIG. 4B) through the tissue defining wound bed "w" and thereby aid in the treatment/healing thereof.

Figure 5A:
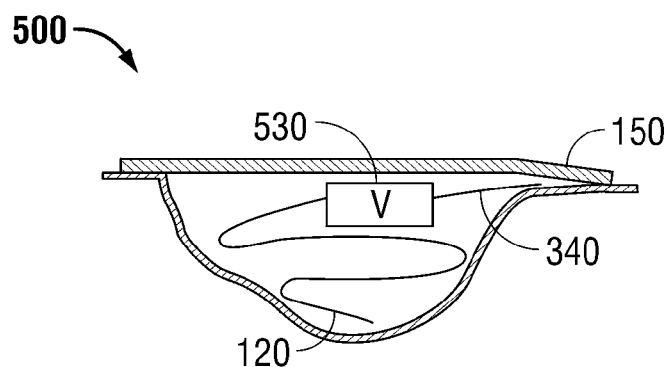
FIG. 5A is a side cross-sectional view of a wound dressing system including a voltage source disposed in a first location, in accordance with the present disclosure.

Referring now to FIG. 5A, a method of using and applying wound electrode 120 and wound dressing system 100, illustrating a positioning of a voltage source 530, in accordance with the present disclosure is depicted. Wound dressing system 500 is substantially similar to wound dressing system 100 and thus will only be discussed in detail herein to the extent necessary to describe the construction and/or use thereof.

Wound dressing system 500 includes cover layer 150 for covering bed "w," and a voltage source 530 is positioned within wound bed "w." As seen in FIG. 5A, voltage source 530 is placed in wound bed "w," above wound electrode 120 and captured by or beneath layer cover layer 150.

The connecting or conducting wires 140, 342 of wound electrode 120 and peri-wound electrode 340, respectively, forming connecting wire 330 and coming out of rotator 320 are connected to voltage source 530 by a suitable connector 460. Voltage source 530 provides DC, pulsed DC, AC or any other suitable current, appropriate for a particular patient, to conducting wires 140, 342. Voltage source 530 may be an electromechanical device controlled by means of embedded software so as to provide a current profile desired by the clinician. This externally applied current mimics and enhances the naturally occurring flow of electrical current generated by the injured bodily tissue, and thus augments the wound healing process.

Figure 5B:
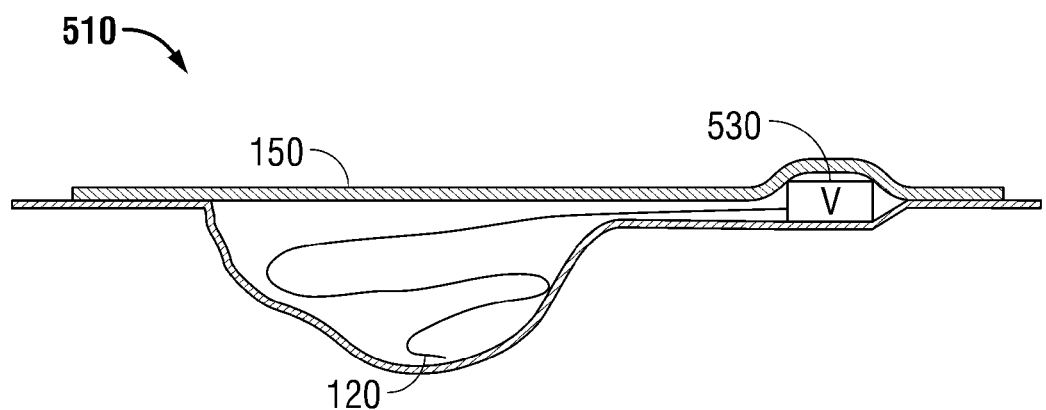
FIG. 5B is a side cross-sectional view of a wound dressing system including a voltage source disposed in a second location, in accordance with the present disclosure.

Referring now to FIG. 5B, a method of using and applying wound electrode 120 and wound dressing system 100, illustrating a positioning of a voltage source 530, in accordance with the present disclosure is depicted. Wound dressing system 500 is substantially similar to wound dressing system 100 and thus will only be discussed in detail herein to the extent necessary to describe the construction and/or use thereof.

In the embodiment of FIG. 5B, voltage source 530 is affixed in the peri-wound region in close proximity to the peri-wound electrode 340 by placing some section of the cover layer above and around it.

It is contemplated that wound electrode 120 may act as a positive energy pole and peri-wound electrode 340 may act as a negative energy pole, or vice-versa, to thereby create a current path therebetween and create a therapeutic effect on the surface of wound bed "w" to enhance the healing process thereof. It is envisioned that the current may be continuously applied, applied in pulses, applied for specific periods of time or combination thereof.

In accordance with an aspect of the present disclosure, it is envisioned that the plurality of hydrogel beads may be connected in a strand by a non-conductive wire, filament, line, thread or the like. By having a plurality of hydrogel beads that are connected in a strand allows an end user (e.g., surgeon, nurse, etc.) to better pack a wound with a plurality of hydrogel beads and to also allow for the remnants of the plurality of hydrogel beads, following their useful life or some predetermined period of time, to be more easily removed from the wound since the plurality of hydrogel beads are connected in a strand.

In any of the preceding embodiments described herein, the present disclosure may relate to a patient monitoring system which provides enhanced functional capability relative to known systems and provides a wireless communication link between a patient monitoring device, worn by a patient, and a local hub. The patient monitoring system may be adapted to monitor various patient physiological characteristics. The data from the patient monitoring device may be wirelessly transmitted to a local hub, which, in turn, is configured to automatically transfer the data to a remote server or computer (e.g., of a clinician), for example, over a public or private communications network.

It is to be understood that the illustrated embodiments are for the purpose of example, and that numerous other configurations of wound dressing systems having a plurality of beads exist. Accordingly, the illustrated and described embodiments are not intended to limit the scope of the inventive subject matter only to those embodiments.

Although the illustrative embodiments of the present disclosure have been described herein with reference to the accompanying drawings, it is to be understood that the disclosure is not limited to those precise embodiments, and that various other changes and modifications may be effected therein by one skilled in the art without departing from the scope or spirit of the disclosure.

Those skilled in the art, having the benefit of the teachings of the present invention as herein and above set forth, may effect modifications thereto. Such modifications are to be construed as lying within the scope of the present invention, as defined by the appended claims.

Although specific features of the wound dressing system are shown in some of the drawings and not in others, this is for convenience only as each feature may be combined with any or all of the other features in accordance with the aspects of the present disclosure. Other embodiments will occur to those skilled in the art and are within the following claims.

What is claimed is:

1. A method of manufacturing a wound dressing, the method comprising the steps of:
   providing a cover layer, wherein the cover layer is configured for positioning across a wound and is configured to permit exudates from the wound to pass therethrough;
   providing an elongate member positionable in the wound, comprising adjacent beads connected to each other by connecting segments,
   the beads and the connecting segments comprising a hydrogel material; and
   providing an electrode extending through at least some of the beads and through the connecting segments along a length of the elongate member;
   wherein a current generated by an energy source electrically flows through the electrode.

2. The method according to claim 1, further comprising providing a conduit for supplying reduced pressure to the wound.

3. The method according to claim 1, wherein the electrode extends through an entire length of the elongate member.

4. The method according to claim 1,
   wherein each bead of the plurality of beads has a first length;
   wherein adjacent beads of the plurality of beads are separated from each other by a second length; and
   wherein the first length is greater than the second length.

5. The method according to claim 1, wherein a portion of at least one bead of the plurality of beads includes a conductive coating.

6. The method according to claim 5, wherein the conductive coating is at least one of Ag, Ag/AgCl, Cu, Au, carbon rubber, carbon film, and aluminum film.

7. The method according to claim 1, further comprising providing a peripheral electrode and a rotator in operable communication with the peripheral electrode.

8. The method according to claim 1, wherein the energy source is embedded within the cover layer.

9. The method according to claim 8, wherein the energy source is positioned at one end of the elongate member.

10. The method according to claim 8, wherein the energy source is positioned so as to divide the elongate member into at least two portions.

11. The method according to claim 1, wherein each of the plurality of beads is sufficiently rigid to facilitate passage of the exudates through spaces defined between adjacent beads.

\* \* \* \* \*